(12) United States Patent
Reykhert

(10) Patent No.: US 11,013,433 B1
(45) Date of Patent: May 25, 2021

(54) GLUCOSE MONITORING SYSTEM

(71) Applicant: ANEXA LABS LLC, Mountain View, CA (US)

(72) Inventor: Alexey Reykhert, Omsk (RU)

(73) Assignee: Anexa Labs LLC, Mountain View, CA (US)

( * ) Notice: Subject to any disclaimer, the term of this patent is extended or adjusted under 35 U.S.C. 154(b) by 0 days.

(21) Appl. No.: 16/776,283

(22) Filed: Jan. 29, 2020

(51) Int. Cl.
*A61B 5/145* (2006.01)
*A61B 5/0408* (2006.01)
*A61B 5/024* (2006.01)

(52) U.S. Cl.
CPC ...... *A61B 5/14532* (2013.01); *A61B 5/02427* (2013.01); *A61B 5/0408* (2013.01)

(58) Field of Classification Search
None
See application file for complete search history.

(56) References Cited

U.S. PATENT DOCUMENTS

| | | | | |
|---|---|---|---|---|
| 5,741,211 A | * | 4/1998 | Renirie | A61B 5/14532 600/300 |
| 5,792,668 A | * | 8/1998 | Fuller | A61B 5/053 324/642 |
| 2007/0060802 A1 | * | 3/2007 | Ghevondian | A61B 5/0002 600/301 |
| 2008/0228045 A1 | * | 9/2008 | Gao | A61B 5/0024 600/301 |
| 2017/0164878 A1 | * | 6/2017 | Connor | A61B 5/053 |

OTHER PUBLICATIONS

Porumb, M. et al.; Precision medicine and artificial intelligence: a pilot study on deep learning for hypoglycemic events detection based on ECG; Nature, 2020, 10:170, 16 pages.
Sobel, S.I. et al.; Accuracy of a novel noninvasive multisensor technology to estimate glucose in diabetic subjects during dynamic conditions; Journal of Diabetes Science and Technology, 2014, vol. 8(1) 54-63.
Talary, M.S. et al., Non-invasive impedance based continuous glucose monitoring system; ICEBI, 2007, IFMBE Proceedings 17, pp. 636-637.
Wei, T., et al.; Noninvasive glucose evaluation by human skin oxygen saturation level; 2016 IEEE International Instrumentation and Measurement Technology Conference Proceedings, Taipei, 2016, pp. 1-5, doi: 10.1109/I2MTC.2016.7520571.

\* cited by examiner

*Primary Examiner* — Michael R Bloch
(74) *Attorney, Agent, or Firm* — Nixon Peabody LLP

(57) ABSTRACT

Disclosed herein are systems and methods for non-invasively monitoring blood glucose levels with a level of accuracy that is high enough to replace invasive methods such as finger prick devices and others. In some examples, glucose values are determined using a patient's electrocardiogram (ECG) signals. Additionally, glucose values may additionally be determined using an impedance spectroscopy based method and then combined with glucose values determined using an ECG waveform to output a blood glucose value.

19 Claims, 4 Drawing Sheets

GLUCOSE MONITORING SYSTEM

FIELD

The present invention is directed to glucose monitoring systems.

BACKGROUND

The following description includes information that may be useful in understanding the present invention. It is not an admission that any of the information provided herein is prior art or relevant to the presently claimed invention, or that any publication specifically or implicitly referenced is prior art.

Existing non-invasive glucose monitoring systems have poor accuracy and have not been able to replace devices that require painful finger pricking or other invasive methods such as implants. Accordingly, a need exists in the art for a completely non-invasive glucose monitor with high accuracy.

SUMMARY

Disclosed herein are systems and methods for the non-invasive monitoring of blood glucose levels with a level of accuracy that allows it to replace invasive methods such as finger prick devices and others. In some examples, glucose values are determined using a patient's electrocardiogram (ECG). Additionally, glucose values may additionally be determined using an impedance spectroscopy based method and then combined with glucose values determined using an ECG waveform to output a more accurate blood glucose value.

Accordingly, it has been discovered that blood glucose values may be determined entirely from the ECG waveform. For instance, certain ECG features (e.g. QRS complex, ST segment, QT interval, etc.) were unexpectedly discovered to be closely coherent with the blood glucose value and thus could be utilized to determine a blood glucose value. This is very advantageous, because it allows for a completely non-invasive method of monitoring glucose values with relatively simple sensors (e.g. electrodes) and other hardware that is quite accurate.

Additionally, blood glucose level may also be determined using a resonant frequency based method. An example of an impedance based blood glucose measurement is described by Talary, et al., in "Non-Invasive Impedance based Continuous Glucose Monitoring System," published by IFMBE in 2007, the content of which is incorporated by reference herein in its entirety. This approach also only requires electrodes as a sensor.

Then, the outputs from these two methods may be combined using a linear equation or other methods to get a highly accurate glucose level. This is also advantageous, as the accuracy of the readings may be further improved by combining these methods and outputting an even more accurate value using only electrodes touching a patient's skin. Thus, the entire system only requires electrodes functioning as sensors and voltage appliers, and can output glucose levels that has accuracy approaching or equal to clinical invasive based methods.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
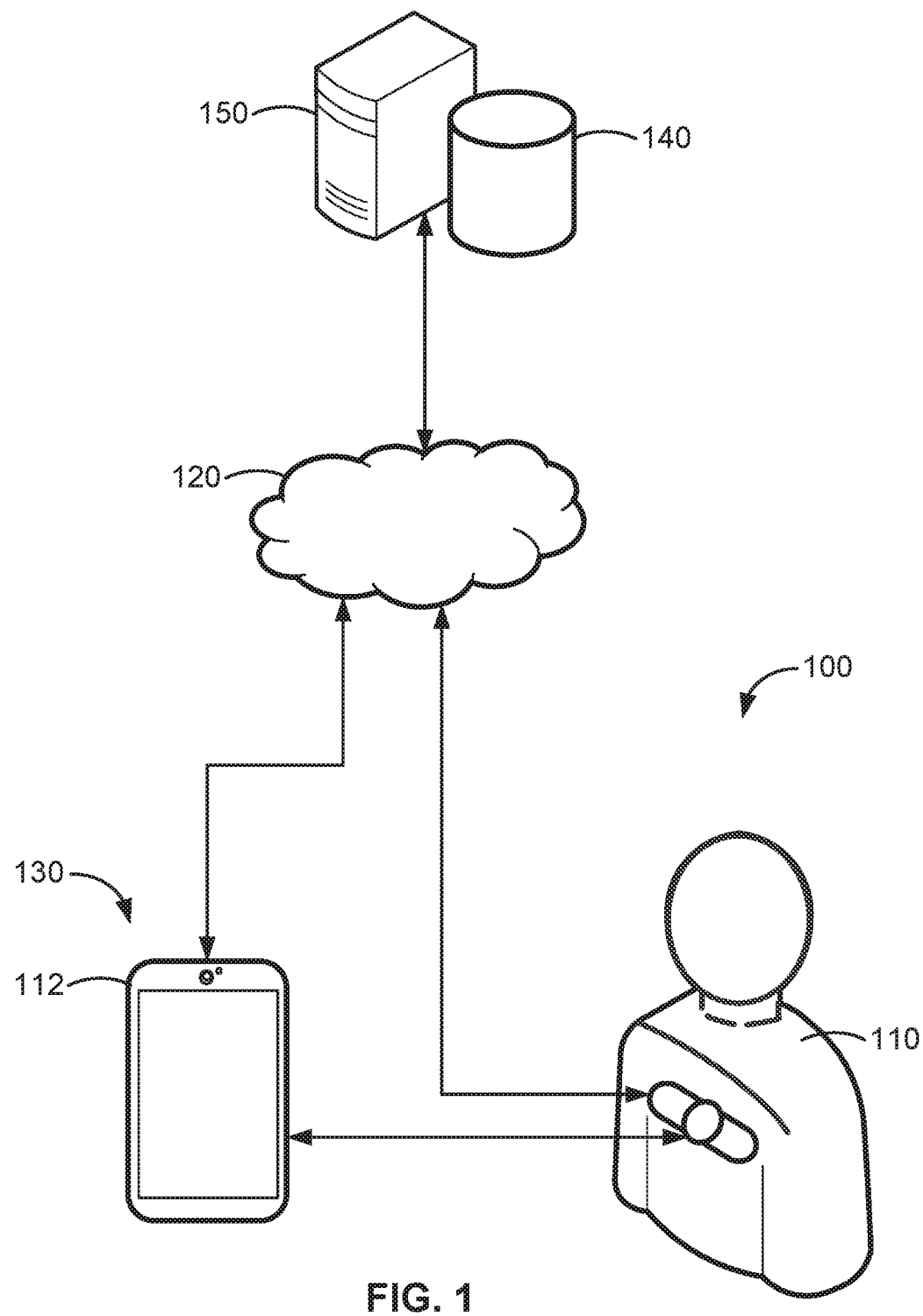
FIG. 1 depicts an example overview of a system for non-invasive glucose monitoring.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Disclosed herein are systems and methods for the non-invasive monitoring of blood glucose levels with a level of accuracy that allows it to replace invasive methods such as finger prick devices and others. In some examples, glucose values are determined using a patient's electrocardiogram (ECG). Additionally, glucose values may additionally be determined using an impedance spectroscopy based method and then combined with glucose values determined using an ECG waveform to output a more accurate blood glucose value.

Accordingly, it has been discovered that blood glucose values may be determined entirely from the ECG waveform. For instance, certain ECG features (e.g. QRS complex, ST segment, QT interval, etc.) were unexpectedly discovered to be closely coherent with the blood glucose value and thus could be utilized to determine a blood glucose value. This is very advantageous, because it allows for a completely non-invasive method of monitoring glucose values with relatively simple sensors (e.g. electrodes) and other hardware that is quite accurate.

Additionally, blood glucose level may also be determined using a resonant frequency based method. An example of an impedance based blood glucose measurement is described by Talary, et al., in "Non-Invasive Impedance based Continuous Glucose Monitoring System," published by IFMBE in 2007, the content of which is incorporated by reference herein in its entirety. This approach also only requires electrodes as a sensor.

Then, the outputs from these two methods may be combined using a linear equation or other methods to get a highly accurate glucose level. This is also advantageous, as the accuracy of the readings may be further improved by combining these methods and outputting an even more accurate value using only electrodes touching a patient's skin. Thus, the entire system only requires electrodes functioning as sensors and voltage appliers, and can output glucose levels that has accuracy approaching or equal to clinical invasive based methods.

Systems

FIG. 1 illustrates an example system for implementing the disclosed technology. For instance, the system may contain a computing device 130 with a display 112, a network 120, a patient 100, a wearable 110, a server 150 and database 140. The computing device 130 may be any suitable computing device, including a computer, laptop, mobile phone, etc. The network 120 may be wired, wireless, or various combinations of wired and wireless. The server 150 and database may be local, remote, and may be combinations of servers 150 and databases 140, or could be local processors and memory.

The wearable 110 may be a smart watch, smart ankle bracelet, smart glasses, smart ring, patch, band, digital stethoscope, or other device that suitably could be retained on the patient 100 and give access to the patient's 100 skin to various sensors on the wearable 110. In some examples, the wearable 110 may include adhesive and stick onto a patient's 100 skin on the neck, chest, arm, leg, torso, back or other suitable locations. In other examples, the wearable 110 may be a clinical grade ECG system and the glucose values may be determined in a hospital using clinical grade ECG equipment and electrodes to determine the values non-invasively.

Figure 2:
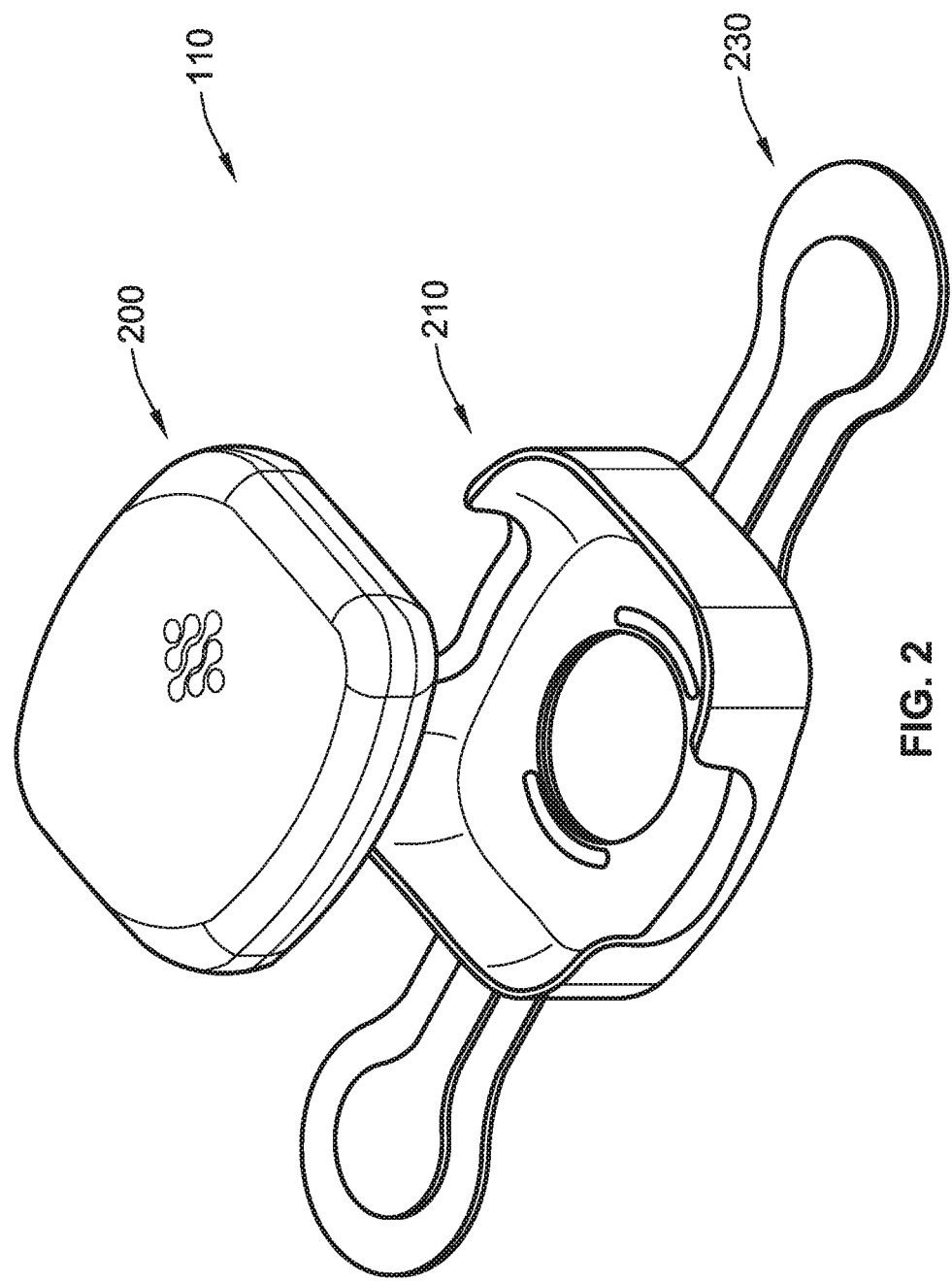
FIG. 2 depicts an example overview of a patch for non-invasive glucose monitoring.

FIG. 2 provides an example overview of the wearable 110. The wearable 110 may include a sensor module 200, a cradle 210, and electrodes 230. In other examples, the wearable 110 may only include a sensor module 200 and electrodes 230. In still other examples, the wearable 110 may only be electrodes 230 connected to a clinical grade ECG machine. The sensor module 200 may incorporate a wireless transmitter (e.g. Bluetooth, WiFi), various circuit boards, memory, processors and other electrical components and also may include a wired connection to a signal processor. The sensor module 200 may also include electrical contacts that connect to the electrodes.

The sensor module 200 may also include a photoplethysmography ("PPG") sensor that includes LEDs and photodiodes or other optical sensors. Accordingly, the PPG sensor may be utilized to detect the heart rate or blood oxygenation. In some examples, the output of the PPG sensor may be processed to output various peak points of the heart cycle, that include the systolic peak point, diastolic peak point, and the maximum peak point of the venus pulse that correlates to the cardiac cycle. These peak points can be utilized to determine the heart rate based on the time intervals between specific peak points.

The cradle 210 may allow the sensor module 200 to be removably attached from the cradle 210 so that the sensor module 200 could be recharged or cleaned without removing the electrodes 230 from the patient 100. The cradle 210 may attach to the sensor module 200 using a pressure fit, snap, latch, or other suitable methods. In some examples the cradle 210 has a window or opening that allows the PPG sensor on the sensor module 200 to optically detect the heart rate and blood oxygenation.

The electrodes 230 may be any suitable electrodes for detecting electrical signal from a patient's skin, and performing an ECG analysis and/or an impedance spectroscopy analysis. For instance, the electrodes may be adhesive electrodes that attach to the patient's skin. The electrodes 230 may also be any suitable electrodes for use with a clinical grade ECG system. The electrodes 230 may include three electrodes 230 that are equivalent or represent the LA, RA, and RL electrodes of a conventional ECG. In other examples, the system could include five electrodes or other suitable electrode configurations, for example, as described in U.S. Pat. No. 8,200,320 issued to Kovacs, and U.S. Patent Publication No. 2019/0117100 issued to Rollie et al., and U.S. Pat. No. 10,299,691 issued to Hughes, the content of all of which are incorporated by reference in their entirety.

Figure 3:
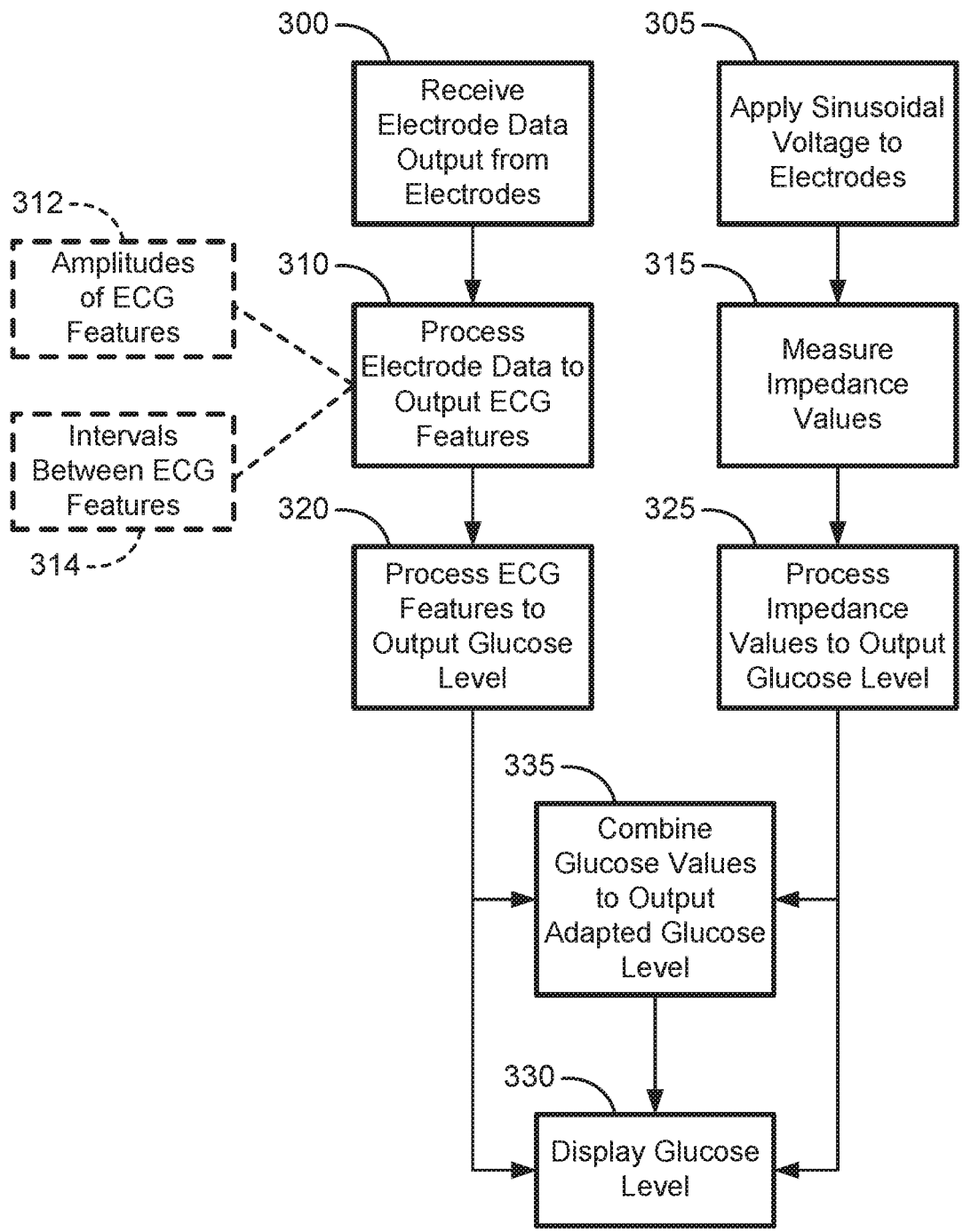
FIG. 3 depicts a flow chart showing an example method for measuring blood glucose.
Figure 4:
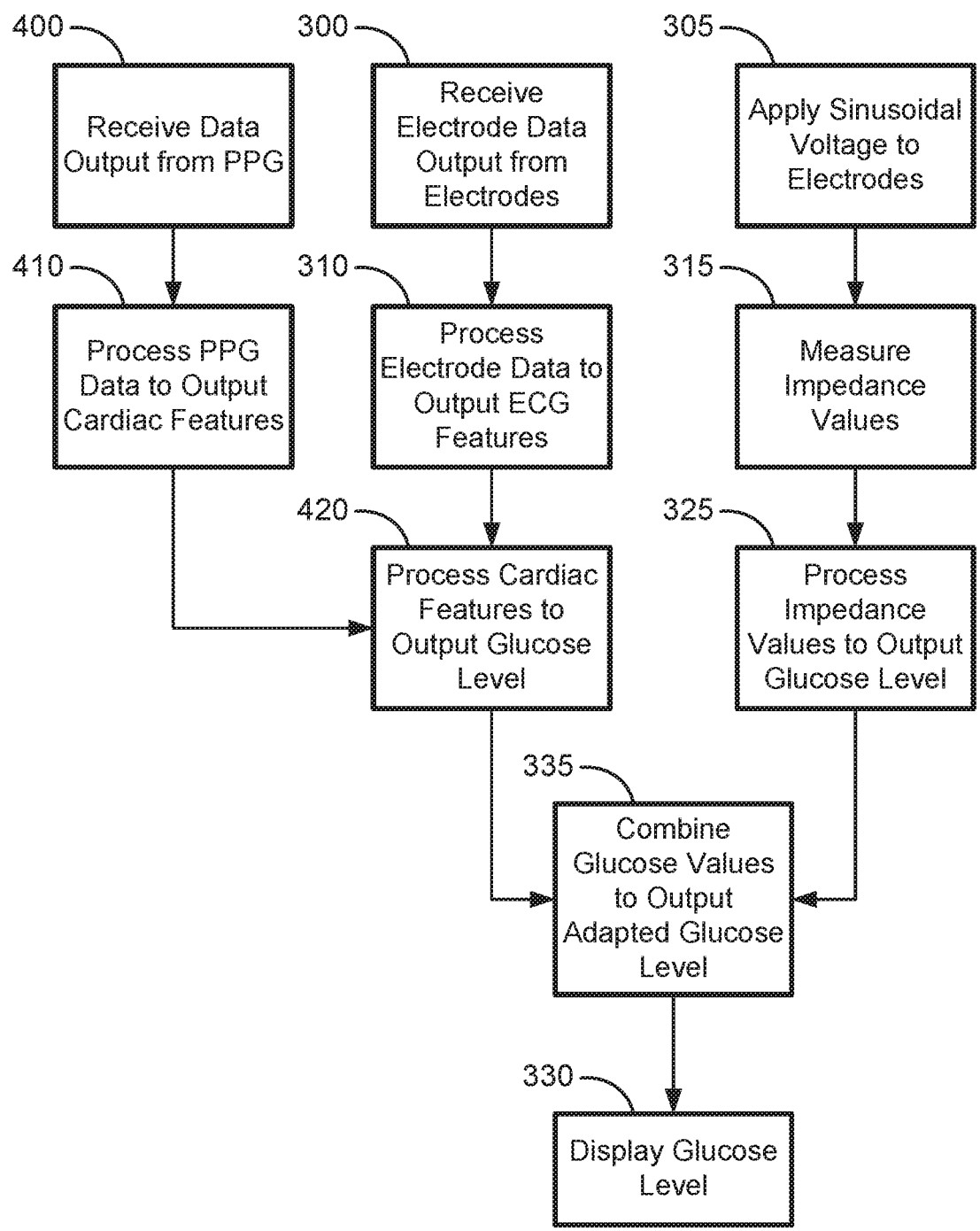
FIG. 4 depicts a flow chart showing an example method for measuring blood glucose.

The system may then be utilized to measure various electrical properties to determine blood glucose values. This includes determining the blood glucose value using: (1) ECG features and (2) impedance based spectroscopy methods. FIGS. 3 and 4 are flowcharts illustrating examples methods of implementing the disclosed technology.

ECG Based Measurement

As illustrated in FIG. 3, the system may determine an ECG based blood glucose value by first receiving electrode data output from the electrodes 300 that represents electrical activity of the heart sensed on the patient's 100 skin. Then, the system may process the electrode data to output ECG features 310.

To process the electrode data into ECG features, the signal may be amplified and filtered (e.g. low-pass filters, notch filters, high-pass filters). For instance, in some examples, a commercially available front end ECG signal conditioner may be utilized, including the AD8232. In this example, front end signal conditioning systems like the AD8232 are designed to extract, amplify and filter small bio-potential signals in the presence of noisy conditions, such as those created by motion of the patient 100 or remote electrode placement. This is particularly advantageous, as the wearable 110 signals from the electrodes may be relatively noisy when the patient 100 or user is moving around as the wearable 110 is designed to continuously or periodically determine blood glucose values at different times of day. Furthermore, front end systems like the AD8232 are additionally advantageous because they can determine whether both of the electrodes are in contact with the skin and can save power by not initiating processing of the ECG signal unless both electrodes 300 are in contact.

The ECG features that may be output 310 include a variety of different time periods, amplitudes and other features. For instance, the features may include amplitude differences 312 between certain landmarks or points on the ECG signal, or time periods/intervals 314 between certain points on the ECG signal. Examples of features include but are not limited to the P wave, QRS complex wave, T wave), 5 feature points (P, Q, R, S, T points), PR interval (time between the beginning of the P wave and the beginning of the QRS complex), the duration of the QRS complex, the ST segment, the QT interval and other suitable ECG features.

In some examples, a QRS complex may be the least noisy signal detected and therefore the Q point may serve as a reference point or reference amplitude to calculate/calibrate the various ECG features 310. Additionally, certain ECG waves, features, and/or points may be too noisy and may be discarded as data points, for instance if they would result in an abnormally large heart rate or would be outside of other normal thresholds.

Next, the system may then process the ECG features to output a blood glucose level 320. This is advantageous, because it has been discovered that the blood glucose level can be determined solely from ECG features. In some instances, processing the ECG features may be performed according to equation 1.

$$\text{Glucose level} = C1*(QS\text{ Amplitude}/QR\text{ amplitude} + TR\text{ Amplitude}/ST\text{ Amplitude}) + C2*(Q\text{-}T\text{ interval}/Q\text{-}S\text{ interval}) \quad \text{Equation 1:}$$

Disclosed herein:
QS Amplitude=amplitude difference between Q and S points;
QR Amplitude=amplitude difference between Q and R points;
TR Amplitude=amplitude difference between T and R points;
ST Amplitude=amplitude difference between S and T points;
Q-T interval=time difference between Q and S points;
Q-S interval=time difference between Q and S points; and The parameters C1 and C2 may be determined during a calibration procedure by acquiring at least two or more sets of data that includes clinical grade clean ECG signals and invasive blood glucose readings taken at the same time from the same patient 100. Experimentation has shown that these coefficient values vary little from person to person, but instead are reliant on the hardware utilized. Accordingly, in some manufacturing methods, once a specific device is tested, the testing data could be utilized to determine the C1 and C2 coefficients for a specific device. In other examples, there could be universal constants determined if the hardware manufacturing process is consistent once it is determined for one or a subset of the devices.

In an example calibration procedure, glucose levels can be measured using an invasive glucose monitor, and a medical grade ECG waveform can be acquired to derive the parameters in Equation 1 at multiple time points. Accordingly, the values recorded at each time point may be inserted into separate equations and then the equations solved to determine the values of the constants:

$$\text{Glucose Level1} = C1*k1 + C2*p1 \quad \text{Equation 2:}$$

$$\text{Glucose Level2} = C1*k2 + C2*p2 \quad \text{Equation 3:}$$

Thus, the parameters k1, p1, and k2, p2 are determined based on the measurement and testing with gold standard equipment and the variables described above. For instance, each of the above variables could be derived with the following measurements:

$k1=(QS\text{ Amplitude}/QR\text{ amplitude} + TR\text{ Amplitude}/ST\text{ Amplitude})$ measured at the time Glucose Level1 is measured $p1=(Q\text{-}T\text{ interval}/Q\text{-}S\text{ interval})$ measured at the time Glucose Level1 is measured $k2=(QS\text{ Amplitude}/QR\text{ amplitude} + TR\text{ Amplitude}/ST\text{ Amplitude})$ measured at the time Glucose Level2 is measured $p2=(Q\text{-}T\text{ interval}/Q\text{-}S\text{ interval})$ measured at the time Glucose Level2 is measured Thus, the above two equations can be solved to identify the parameters C1 and C2. In other examples, additional measurements and equations may be utilized to refine the constants, for instance with 3, 4, 5, 8, or 10 measurements. Accordingly, the values of these constants may be stored in the memory of the device, and may be reused for additionally manufactured devices as long as there are not changes to the devices.

While this specific equation has been shown to output accurate glucose results, various other combinations of the amplitudes 312, intervals 314 and other ECG features may be processed with a linear or other equation to determine blood glucose levels 320.

Next, and as described in greater detail herein, the ECG based blood glucose levels could be combined with the impedance based blood glucose levels 325 to output an adapted glucose level 335 as described in greater detail below. These values could then be displayed 330 and/or stored in a database 140 or provide other various uses.

PPG Signal to Confirm or Estimate Cardiac Features

In some examples, the ECG signal acquired from the electrodes may be too noisy to identify the ECG points and/or features with sufficient accuracy. For instance, the ECG points acquired may result in an abnormally large heart rate, or would be outside of other known physiological thresholds. Accordingly, in some examples as illustrated in FIG. 4, the PPG sensor output 400 may be processed to identify analogous cardiac features 410 that may be utilized to check whether the ECG acquired features are accurate, or to enhance the accuracy of the ECG acquired feature points. The cardiac features may be further processed to output glucose level 420.

Additionally, many of the ECG features utilized include amplitudes of the ECG signal. However, frequently, noise may cause various amplitudes of the EEG signal to be inaccurate. However, the PPG signal has highly accurate peak amplitudes of the cardiac cycle.

Accordingly, these amplitudes may be utilized to calibrate the ECG signal amplitudes, confirm the amplitudes are accurate, reject ECG data that doesn't match within a threshold of the PPG readings, for instance, or replace the ECG amplitudes with certain PPG based amplitude readings. For instance, the maximum PPG amplitude could be utilized to replace the amplitudes related to the QRS complex that are utilized in Equation 1. In some examples, the amplitude of the PPG reading could be correlated to a clinical grade ECG amplitudes to determine an ECG amplitudes from the PPG based amplitudes.

Impedance Spectroscopy Based Measurement

In some examples, the system will determine an impedance based glucose level that can be combined with the ECG based glucose level to output an accurate and adapted glucose level 335 as in FIGS. 3 and 4. An example of an impedance based blood glucose measurement is described by Talary, et al., in "Non-Invasive Impedance based Continuous Glucose Monitoring System," published by IFMBE in 2007, the content of which is incorporated by reference herein in its entirety. The impedance based glucose values may be determined by first applying a sinusoidal voltage to the electrodes 305 and measuring impedance values 315. Then, then impedance values may be processed to output a blood glucose level 325.

The impedance values of the skin are related to blood glucose levels. The values are not static but will change with various frequencies of voltage applied to the skin (e.g. sinusoidal voltages). The impedance values of the skin can be measured by any suitable methods, including by using a voltage divider or a Vector Network Analyzer.

In some examples, a low amplitudes voltage (e.g. <0.3V) will be applied to the electrodes and voltage divider. In other examples various other amplitudes greater than 0.3V could be applied. Additionally, in some examples, the voltage applied will be within the range of 1 MHz-160 MHz, or 10 MHz-200 MHz. In other examples, other frequencies could be utilized.

Specifically, the system may scan the frequencies and detect the resulting impedance in a certain range until the system identifies the lowest impedance value. For instance, the microcontroller may sweep from 10 MHz to 200 MHz frequency range by controlling DAC values from 0 to 1024. In this example, the voltage control unit (VCO) will apply a frequency sweeping through these values every 100μ seconds. In this case, the frequency separation resolution is 100 KHz, so 1900 points could be measured to obtain an impedance response values or graph that could be stored in the database 140, local memory of the patch or other wearable device, or other locations. These values may be calibrated with current temperature values, amplitudes of a QRS complex of an ECG, and heart rate values with a linear equation through experimentation. The lowest impedance value corresponds to the resonant glucose value, which can be converted to a blood glucose level.

Combining the ECG and Impedance Based Blood Glucose Values

Lastly, the impedance based glucose value and the ECG based glucose value may be combined to output an adapted glucose level 335 as depicted in FIGS. 3 and 4. These values may be combined using various equations or methods. In one example, these methods may be combined using the following linear formula:

$$\text{Glucose level} = C3 * \text{impedance glucose level} + C4 * \text{ECG glucose level} \quad \text{Equation 4:}$$

Accordingly, constants C3 and C4 may be determined through experimentation using invasive glucose based level taken simultaneously with measured values of impedance based glucose level and the ECG based glucose level using a device as disclosed herein. Thus, for a particular patient and a particular device, the glucose level could be measured invasively at least two different times, and at each of those times, an impedance based glucose level and an ECG based glucose level could be measured using a device as disclosed herein. Then, the constants could be determined by solving the set of questions derived from those values. In some examples, this could be performed, with 3, 4, 5, 10 or other suitable numbers of measurements to increase the accuracy.

Example: Experimental Data

The disclosed systems and methods were tested on patients and compared to invasive glucose values. For instance, in one example, a prototype device comprising a wearable patch was developed that measured and output glucose levels by determining an adapted glucose level 335 as disclosed herein by combining a measured ECG based glucose value and an impedance based glucose value.

As illustrated in Table 1 below, the test values using the disclosed systems and methods were quite close to the invasive gold standard values of blood glucose measured using the Accu-Chek Performa Blood Glucose Meter and Lancing Device (model number B9BIGGTGO).

| Patient | Test Glucose (mmol/L) | Real Glucose (mmol/L) | Difference (mmol/L) | Percent Difference |
|---|---|---|---|---|
| 1 | 5.3 | 5.1 | 0.2 | 3.92% |
| 2 | 6.8 | 7 | 0.2 | 2.86% |
| 3 | 3.4 | 3.8 | 0.4 | 10.53% |
| 4 | 5.1 | 5.4 | 0.3 | 5.56% |
| 5 | 10.7 | 10.4 | 0.3 | 2.88% |
| 6 | 6.2 | 6.3 | 0.1 | 1.59% |
| 7 | 3.1 | 3.7 | 0.6 | 16.22% |
| 8 | 5.9 | 6.2 | 0.3 | 4.84% |
| 9 | 6.5 | 6.5 | 0 | 0.00% |
| 10 | 7.8 | 7.4 | 0.4 | 5.41% |
| 11 | 5.2 | 5.4 | 0.2 | 3.70% |
| 12 | 9.4 | 9.5 | 0.1 | 1.05% |
| 13 | 9.2 | 9.6 | 0.4 | 4.17% |
| 14 | 4.2 | 4.5 | 0.3 | 6.67% |
| 15 | 4.6 | 4.3 | 0.3 | 6.98% |
| 16 | 6.7 | 6.5 | 0.2 | 3.08% |
| 17 | 7 | 7.1 | 0.1 | 1.41% |
| 18 | 5.7 | 5.4 | 0.3 | 5.56% |
| 19 | 3.2 | 3.7 | 0.5 | 13.51% |
| 20 | 2.8 | 3.1 | 0.3 | 9.68% |
| 21 | 5.8 | 5.7 | 0.1 | 1.75% |
| 22 | 5.4 | 5.2 | 0.2 | 3.85% |
| 23 | 9.7 | 9.5 | 0.2 | 2.11% |
| 24 | 9.6 | 9.7 | 0.1 | 1.03% |
| 25 | 4.1 | 4.6 | 0.5 | 10.87% |

-continued

| Patient | Test Glucose (mmol/L) | Real Glucose (mmol/L) | Difference (mmol/L) | Percent Difference |
|---|---|---|---|---|
| 26 | 5.3 | 5.1 | 0.2 | 3.92% |
| 27 | 3.7 | 3.8 | 0.1 | 2.63% |
| 28 | 6.5 | 6.4 | 0.1 | 1.56% |
| 29 | 6.4 | 6.2 | 0.2 | 3.23% |
| 30 | 6.9 | 7 | 0.1 | 1.43% |
| 31 | 6.2 | 6.2 | 0 | 0.00% |
| 32 | 5.3 | 5.1 | 0.2 | 3.92% |
| 33 | 6.8 | 7 | 0.2 | 2.86% |
| 34 | 3.4 | 3.8 | 0.4 | 10.53% |
| 35 | 5.1 | 5.4 | 0.3 | 5.56% |
| 36 | 10.7 | 10.4 | 0.3 | 2.88% |
| 37 | 6.2 | 6.3 | 0.1 | 1.59% |
| 38 | 3.1 | 3.7 | 0.6 | 16.22% |
| 39 | 5.9 | 6.3 | 0.4 | 6.35% |
| 40 | 6.5 | 6.5 | 0 | 0.00% |
| 41 | 6.1 | 6.3 | 0.2 | 3.17% |
| 42 | 9.4 | 9.5 | 0.1 | 1.05% |
| 43 | 9.2 | 9.6 | 0.4 | 4.17% |
| 44 | 5.7 | 5.4 | 0.3 | 5.56% |
| 45 | 4.2 | 4.5 | 0.3 | 6.67% |
| 46 | 3.2 | 3.7 | 0.5 | 13.51% |
| 47 | 5.8 | 5.4 | 0.4 | 7.41% |
| 48 | 6.7 | 6.5 | 0.2 | 3.08% |
| 49 | 7 | 7.2 | 0.2 | 2.78% |
| 50 | 3.7 | 3.9 | 0.2 | 5.13% |
| Average for 50 Patients | 6.05 | 6.14 | | 4.89% |

Accordingly, this experimental data illustrated there was only an average of about a 5% difference between the tested glucose value using the patch based prototype according to the methods disclosed herein and the invasive based glucose value.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, a wearable device, a digital stethoscope, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks), and any wireless networks.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, flash memory, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, multi-core processors, GPUs, AI-accelerators, In-memory computing architectures or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures, and deep learning and artificial intelligence computing infrastructure.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, flash memory or optical disks. However, a computer need not have such devices. Moreover, a computer can be embedded in another device, e.g., a mobile telephone, a personal digital assistant (PDA), smart watch, smart glasses, patch, wearable devices, a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

SELECTED EMBODIMENTS

Although the above description and the attached claims disclose a number of embodiments of the present invention, other alternative aspects of the invention are disclosed in the following further embodiments.

Embodiment 1

A system for monitoring glucose values of a patient, the system comprising: at least two electrodes configured to output electrical data; a display; a memory; a control system coupled to the memory comprising one or more processors, the control system configured to execute the machine executable code to cause the control system to: receive a set of electrical data output from the at least two electrodes; process the set of electrical data to output a set of electrocardiogram features; and process the set of electrocardiogram features to output an ECG-based blood glucose level; and store the ECG-based blood glucose level in the memory.

Embodiment 2

The system of embodiment 1, wherein the set of electrocardiogram features comprises amplitude differences between electrocardiogram points.

Embodiment 3

The system of embodiment 1, wherein the set of electrocardiogram features comprises a QS amplitude, a QR amplitude, a TR amplitude, and an ST amplitude.

Embodiment 4

The system of embodiment 3, wherein the set of electrocardiogram features further comprises a Q-T interval and a Q-S interval.

Embodiment 5

The system of embodiment 4, wherein process the set of electrocardiogram features further comprises process the electrocardiogram features according to the equation $C1*$(the QS Amplitude/the QR amplitude+the TR Amplitude/the ST Amplitude)+$C2*$(the Q-T interval/the Q-S interval).

Embodiment 6

The system of embodiment 5, wherein C1 and C2 are determined by experimentation using a data set output from an invasive glucose meter reading.

Embodiment 7

The system of embodiment 1, further comprising an accelerometer configured to output acceleration data and wherein the control system is further configured to: receive a set of acceleration data output from the accelerometer; and determine an orientation of the user.

Embodiment 8

The system of embodiment 7, wherein process the set of electrical data to output a set of electrocardiogram features further comprises process the orientation of the user.

Embodiment 9

The system of embodiment 1, further comprising an electronic control system connected to the at least two electrodes and configured to control a voltage applied to the electrodes.

Embodiment 10

The system of embodiment 9, wherein the voltage comprises a sinusoidal voltage.

Embodiment 11

The system of embodiment 10, wherein the control system is further configured to: provide instructions to the electronic control system to apply a sinusoidal voltage to the at least two electrodes; determine a set of impedance measurements based on electrical data output from the at least two electrodes; and process the set of impedance measurements to output an impedance-based glucose value.

Embodiment 12

The system of embodiment 11, wherein apply a sinusoidal voltage comprises applying a set of sinusoidal frequencies in the range of 10 MHz-200 MHz.

Embodiment 13

The system of embodiment 11, wherein process the set of impedance measurements to output an impedance-based glucose value further comprises calibration with temperature values, amplitudes of QRS complex values, and heart rate values using a linear equation.

Embodiment 14

The system of embodiment 11, wherein the control system is configured to process the impedance-based glucose value and ECG-based glucose value to output an adapted glucose value.

Embodiment 15

The system of embodiment 14, wherein process the impedance-based glucose value and ECG-based glucose value to output an adapted glucose value comprises combining the impedance-based glucose value and the ECG-based glucose value with a linear formula.

Embodiment 16

The system of embodiment 15, wherein the linear formula comprises summing the impedance-based glucose value multiplied by a first coefficient with the ECG-based glucose value multiplied by a second coefficient.

Embodiment 17

A system for monitoring glucose values of a patient, the system comprising: at least two electrodes configured to output electrical data; a display; a memory; a control system coupled to the memory comprising one or more processors, the control system configured to execute the machine executable code to cause the control system to: receive a set of electrical data output from the at least two electrodes; process the set of electrical data to output a set of electrocardiogram features; process the set of electrocardiogram features to output an ECG-based blood glucose level; and display the ECG-based blood glucose level on the display.

Embodiment 18

A system for monitoring glucose values of a patient, the system comprising: at least two electrodes configured to output electrical data; a display; a memory; a control system coupled to the memory comprising one or more processors, the control system configured to execute the machine executable code to cause the control system to: receive a set of electrical data output from the at least two electrodes; process the set of electrical data to output a set of electrocardiogram features; process the set of electrocardiogram features to output a set of clean electrocardiograph features; emit light into a tissue site of the patient with an emitter; receive a set of optical data output from a set of photodiodes representing light reflected from the tissue site from the emitter; process the set of optical data to determine a set of PPG-based cardiac features; process the set of PPG-based cardiac features and the set of clean electrocardiogram features to output a glucose level; display the glucose level on the display.

Embodiment 19

The system of embodiment 18, wherein the control system is further configured to: provide instructions to the electronic control system to apply a sinusoidal voltage to the at least two electrodes; determine a set of impedance measurements based on electrical data output from the at the at least two electrodes; and process the set of impedance measurements to output an impedance-based glucose value.

Embodiment 20

The system of embodiment 19, wherein the control system is further configured to process the impedance-based glucose value and the glucose level to output an adapted glucose level.

Embodiment 21

The system of embodiment 20, wherein the process the impedance-based glucose level and the glucose level to output an adapted glucose level is performed using linear regression.

Embodiment 22

The system of embodiment 18, wherein process the set of electrocardiogram features to output a set of clean electrocardiograph features comprises eliminating electrocardiogram features in the set of electrocardiogram features that are outside a threshold.

Embodiment 23

The system of embodiment 18, wherein process the set of electrocardiogram features to output a set of clean electrocardiograph features comprises eliminating any features in the set of electrocardiogram features that have a level of noise above a threshold.

Embodiment 24

The system of embodiment 22, wherein process the set of PPG-based cardiac features and the set of clean electrocardiogram features to output a glucose level further comprises replacing the eliminated electrocardiogram features with corresponding PPG-based cardiac features from the set of PPG-based cardiac features.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A system for monitoring glucose values of a patient, the system comprising:
    at least two electrodes configured to output electrical data;
    a display;
    a memory;
    a control system coupled to the memory comprising one or more processors, the control system configured to execute a machine executable code to cause the control system to:
        receive a set of electrical data output from the at least two electrodes;
        process the set of electrical data to output a set of electrocardiogram (ECG) features; and
        process the set of ECG features to output a set of clean ECG features;
        process the set of clean ECG features to output an ECG-based blood glucose level;
        store the ECG-based blood glucose level in the memory; and
        process an impedance-based glucose value and the ECG-based blood glucose level to output an adapted glucose value;
    wherein process the set of ECG features to output a set of clean ECG features comprises eliminating ECG features in the set of ECG features that are outside a threshold; and
    wherein process the set of clean ECG features to output the ECG-based blood glucose level comprises determining the ECG-based blood glucose level based on a function of amplitude difference ratios of the set of clean ECG features and time difference ratios of the set of clean ECG features.

2. The system of claim 1, wherein the control system is further configured to display the ECG-based blood glucose level and/or the adapted glucose value on the display.

3. The system of claim 1, wherein the set of ECG features comprises amplitude differences between ECG points.

4. The system of claim 1, wherein the set of ECG features comprises a QS amplitude difference, a QR amplitude difference, a TR amplitude difference, and an ST amplitude difference; wherein the QS amplitude difference is a difference between Q and S ECG points; wherein the QR amplitude difference is a difference between Q and R ECG points; wherein the TR amplitude difference is a difference between T and R ECG points; and wherein the ST amplitude difference is a difference between S and T ECG points.

5. The system of claim 4, wherein the set of ECG features further comprises a Q–T interval and a Q–S interval.

6. The system of claim 5, wherein process the set of ECG features further comprises process the ECG features according to an equation C1*(the QS Amplitude difference/the QR amplitude difference+the TR Amplitude difference/the ST Amplitude difference)+C2*(the Q–T interval/the Q–S interval); wherein C1 and C2 are determined by experimentation using a data set output from an invasive glucose meter reading.

7. The system of claim 1, further comprising an accelerometer configured to output acceleration data and wherein the control system is further configured to:
receive a set of acceleration data output from the accelerometer; and determine an orientation of the patient.

8. The system of claim 1, further comprising an electronic control system connected to the at least two electrodes and configured to control a voltage applied to the at least two electrodes.

9. The system of claim 8, wherein the voltage comprises a sinusoidal voltage.

10. The system of claim 8, wherein the control system is further configured to:
provide instructions to the electronic control system to apply a sinusoidal voltage to the at least two electrodes;
determine a set of impedance measurements based on electrical data output from the at least two electrodes; and
process the set of impedance measurements to output the impedance-based glucose value.

11. The system of claim 10, wherein apply the sinusoidal voltage comprises applying a set of sinusoidal frequencies in a range of 10 Mhz-200 Mhz.

12. The system of claim 10, wherein process the set of impedance measurements to output the impedance-based glucose value further comprises calibration with temperature values, amplitudes of QRS complex values, and heart rate values using a linear equation.

13. The system of claim 10, wherein apply the sinusoidal voltage comprises applying a set of sinusoidal frequencies in a range of 1 Mhz-160 MHz.

14. The system of claim 1, wherein process the impedance-based glucose value and the ECG-based blood glucose level to output the adapted glucose value comprises combining the impedance-based glucose value and the ECG-based glucose level with a linear formula.

15. The system of claim 14, wherein the linear formula comprises summing the impedance-based glucose value multiplied by a first coefficient and the ECG-based blood glucose level multiplied by a second coefficient.

16. The system of claim 1, wherein the process the impedance-based glucose level and the ECG-based blood glucose level to output the adapted glucose level is performed using linear regression.

17. A method for monitoring glucose values of a patient, the method comprising:
acquiring, via at least two electrodes, a set of electrical data;
receiving, via a control system, the set of electrical data from the at least two electrodes;
processing, via the control system, the set of electrical data to output a set of ECG features;
processing, via the control system, the set of ECG features to output a set of clean ECG features;
processing, via the control system, the set of clean ECG features to output an ECG-based blood glucose level;
storing the ECG-based blood glucose level in a memory coupled to the control system; and
processing an impedance-based glucose value and the ECG-based blood glucose level to output an adapted glucose value;
wherein processing the set of ECG features to output a set of clean ECG features comprises eliminating ECG features in the set of ECG features that are outside a threshold; and
wherein processing the set of clean ECG features to output the ECG-based blood glucose level comprises determining the ECG-based blood glucose level based on a function of amplitude difference ratios of the set of clean ECG features and time difference ratios of the set of clean ECG features.

18. The method of claim 17, wherein the set of ECG features comprises a QS amplitude difference, a QR amplitude difference, a TR amplitude difference, and an ST amplitude difference; wherein the QS amplitude difference is a difference between Q and S ECG points; wherein the QR amplitude difference is a difference between Q and R ECG points; wherein the TR amplitude difference is a difference between T and R ECG points; and wherein the ST amplitude difference is a difference between S and T ECG points.

19. The method of claim 18, wherein processing the set of ECG features further comprises processing the ECG features according to an equation C1*(the QS Amplitude difference/the QR amplitude difference+the TR Amplitude difference/the ST Amplitude difference)+C2*(a Q–T interval/a Q–S interval); wherein C1 and C2 are determined by experimentation using a data set output from an invasive glucose meter reading.

* * * * *